United States Patent
Vollmer et al.

(10) Patent No.: US 9,241,657 B2
(45) Date of Patent: Jan. 26, 2016

(54) MEDICAL IMAGE REGISTRATION USING A RIGID INNER BODY SURFACE

(75) Inventors: Fritz Vollmer, Münich (DE); Manuel Hoever, Münich (DE)

(73) Assignee: Brainlab AG, Feldkirchen (DE)

( * ) Notice: Subject to any disclaimer, the term of this patent is extended or adjusted under 35 U.S.C. 154(b) by 0 days.

(21) Appl. No.: 13/805,830

(22) PCT Filed: Jun. 30, 2010

(86) PCT No.: PCT/EP2010/059245
§ 371 (c)(1),
(2), (4) Date: Dec. 20, 2012

(87) PCT Pub. No.: WO2012/000542
PCT Pub. Date: Jan. 5, 2012

(65) Prior Publication Data
US 2013/0102893 A1     Apr. 25, 2013

(51) Int. Cl.
*A61B 5/05* (2006.01)
*A61B 5/107* (2006.01)
(Continued)

(52) U.S. Cl.
CPC .............. *A61B 5/1076* (2013.01); *A61B 5/0062* (2013.01); *A61B 5/0084* (2013.01);
(Continued)

(58) Field of Classification Search
CPC .... A61B 19/52; A61B 19/5244; A61B 19/20; A61B 19/5212; A61B 6/032; A61B 5/1076; A61B 19/203; A61B 2019/505; A61B 2019/5231; A61B 2019/5255; A61B 2019/5265; A61B 2019/5268; A61B 2019/5272; A61B 2019/5289; A61B 5/0062; A61B 5/0084; A61B 5/055; A61B 5/061; A61B 5/062

USPC .................................. 600/407–430; 606/130
See application file for complete search history.

(56) References Cited

U.S. PATENT DOCUMENTS 6,006,126 A * 12/1999 Cosman .......................... 600/426
6,167,295 A * 12/2000 Cosman .......................... 600/426
(Continued)

FOREIGN PATENT DOCUMENTS

| EP | 1 219 260 | 7/2002 |
| WO | 2004/000097 | 12/2003 |

OTHER PUBLICATIONS

International Search Report for International Application No. PCT/EP2010/059245 dated Mar. 24, 2011.
(Continued)

*Primary Examiner* — Sanjay Cattungal
(74) *Attorney, Agent, or Firm* — Tucker Ellis, LLP

(57) ABSTRACT

The invention relates to a medical image registration method in which an actual patient's body or portion of a patient's body (22) is positionally registered to a patient image created using a medical body-imaging technique such as MR, CT or x-ray imaging, wherein in a medical navigation system, the actual spatial position of at least a part of the body or body portion (22) is assigned to a respective position in the image of said body or body portion (22), wherein the part of the body or body portion (22) comprises a registration area in the form of the surface of a substantially rigid body structure, in particular an inner structure, made of bone or cartilage. The invention also relates to a medical image registration device which comprises a surface scanner (15) for scanning a registration area comprising the surface of a substantially rigid body structure, in particular an inner structure, made of bone or cartilage.

14 Claims, 2 Drawing Sheets

(51) Int. Cl.
*A61B 19/00* (2006.01)
*A61B 5/00* (2006.01)
*A61B 5/055* (2006.01)
*A61B 5/06* (2006.01)
*A61B 6/00* (2006.01)
*A61B 6/03* (2006.01)

(52) U.S. Cl.
CPC ............... *A61B 5/055* (2013.01); *A61B 5/061* (2013.01); *A61B 5/062* (2013.01); *A61B 6/00* (2013.01); *A61B 6/032* (2013.01); *A61B 19/203* (2013.01); *A61B 19/5244* (2013.01); *A61B 2019/505* (2013.01); *A61B 2019/5231* (2013.01); *A61B 2019/5255* (2013.01); *A61B 2019/5265* (2013.01); *A61B 2019/5268* (2013.01); *A61B 2019/5272* (2013.01); *A61B 2019/5289* (2013.01)

(56) References Cited

U.S. PATENT DOCUMENTS

| | | | |
|---|---|---|---|
| 6,259,943 | B1 | 7/2001 | Cosman et al. |
| 6,347,240 | B1 | 2/2002 | Foley et al. |
| 7,327,865 | B2* | 2/2008 | Fu et al. .................. 382/128 |
| 8,675,939 | B2* | 3/2014 | Moctezuma de la Barrera .................. 382/131 |
| 2002/0151907 | A1 | 10/2002 | Day et al. |
| 2003/0131852 | A1 | 7/2003 | Shafer et al. |
| 2004/0015176 | A1 | 1/2004 | Cosman |
| 2005/0222793 | A1 | 10/2005 | Lloyd et al. |
| 2006/0002601 | A1* | 1/2006 | Fu et al. .................. 382/132 |
| 2006/0074292 | A1* | 4/2006 | Thomson et al. .............. 600/411 |
| 2006/0173357 | A1 | 8/2006 | Vilsmeier et al. |
| 2007/0127756 | A1 | 6/2007 | Slabaugh et al. |
| 2008/0130930 | A1 | 6/2008 | Reithinger |
| 2008/0137949 | A1 | 6/2008 | Zouhar et al. |
| 2008/0159612 | A1* | 7/2008 | Fu et al. .................. 382/131 |
| 2009/0285356 | A1* | 11/2009 | Thoma et al. .................. 378/20 |
| 2010/0160771 | A1 | 6/2010 | Gielen et al. |
| 2010/0191510 | A1* | 7/2010 | Kopelman .................. 703/1 |
| 2010/0328304 | A1* | 12/2010 | Kim .................. 345/419 |
| 2011/0152675 | A1* | 6/2011 | Thoma et al. .................. 600/425 |
| 2012/0015316 | A1* | 1/2012 | Sachdeva et al. .................. 433/24 |
| 2012/0033228 | A1* | 2/2012 | Tschudi et al. .................. 356/511 |
| 2012/0092461 | A1* | 4/2012 | Fisker et al. .................. 348/46 |
| 2012/0095732 | A1* | 4/2012 | Fisker et al. .................. 703/1 |
| 2014/0094694 | A1* | 4/2014 | Moctezuma De La Barrera .................. 600/424 |

OTHER PUBLICATIONS

Bankman, "Handbook of Medical Imaging—Processing and Analysis", Handbook of Medical Imaging Processing and Analysis, Jan. 2000, pp. 623-633.

* cited by examiner

MEDICAL IMAGE REGISTRATION USING A RIGID INNER BODY SURFACE

This application is a national phase of International Application No. PCT/EP2010/059245 filed Jun. 30, 2010 and published in the English language.

The present invention relates to a medical image registration method and device. In medical image registration, an actual patient's body or portion of a patient's body is positionally registered to a patient image created using a medical body-imaging technique such as for example MR, CT or x-ray imaging. In most cases, a medical navigation system is used to assign the actual spatial position of at least a part of the body or body portion to a respective position in the image of said body or body portion.

In accordance with the prior art, registration devices are imaged together with the body or body portion, and the images of said registration devices are then used to register the patient to the image of the patient by assigning the images to their actual spatial positions or equivalents. Once such registration method is for example described in DE 196 39 615 A1.

A registration device which is embodied as a dental-based stereotactic localiser is known from US 2004/0015176 A1, and a surgical face mask which is used as a registration device is disclosed in US 2003/0131852 A1.

While registration on the basis of body landmarks (eye canthus, nasion) alone is error-prone when used on its own (due for example to skin movement), registration methods using the registration devices described above are often complicated because the devices have to be fixed on the patient during the imaging step and it is necessary to ensure that they are situated at the same location during the actual registration step. This necessitates either invasive procedures or at least an uncomfortable rigid fixation. Such registration devices are also difficult to keep sterilised, expensive and in many cases difficult to handle.

It is the object of the present invention to provide an image registration method and device which overcome the disadvantages of the prior art. In particular, the intention is to provide an easy-to-use registration method and device which nonetheless still offer optimum registration accuracy. This object is achieved by a medical image registration method in accordance with claim 1 and a medical image registration device in accordance with claim 10. The sub-claims define advantageous embodiments of the invention.

In accordance with the method of the present invention, the part of the body or body portion (which is used for registration) comprises a registration area in the form of the surface of a substantially rigid body structure, in particular an inner structure, made of bone or cartilage. In other words, the present invention moves from using a device fixed on the body or body portion to using a specific part of said body or body portion, namely a part which—as recognised by the invention—is particularly qualified or suitable for this purpose. Registration devices in accordance with the prior art generate reproducible registration points or areas, whereas the present invention has recognised that such reproducible points or areas, i.e. uniquely recognisable registration points or areas, are in fact already provided by certain locations of the body or body portion itself, namely body surfaces or surface areas which have a substantially rigid body structure, in particular an inner structure, made of bone or cartilage. Using currently available surface scanning equipment, such body structures or areas can be imaged to a sufficient level of accuracy that they can be used as registration areas. On the basis of this, the present invention can render the use of separate registration devices unnecessary in many applications. All of the difficulties in handling and problems with inaccuracy associated with the use of such devices can therefore be solved by employing the method of the present invention.

The present invention also enables medical personnel to carry out automatic patient registration, in particular cranial registration, without the need for any additional registration scan, providing the rigid registration area is contained in an image data set which is already available. This is often the case, since such image data sets have usually already been created for diagnostic purposes and are thus available for further use.

Registration in accordance with the present invention will work particularly well with CT and MR imaging methods, thus providing fast and repeatable registration, even during an operation.

In general, the registration area can comprise any sufficiently rigid inner or outer body structure surface, in particular the surface of one or more of the following body structures:
 the meatus or ear channel, or at least a part of the meatus, in particular the outer meatus;
 the palate, in particular the bony or hard palate;
 the upper inner jaw area and/or lower inner jaw area;
 the inner nose cartilage structure.

The registration area or surface can be covered by skin, membrane or mucosa but still able to be determined in terms of its shape.

Such registration areas can in particular be used within the context of cranial patient registration, i.e. within the context of operations involving a patient's head, since most of the bone and/or cartilage structures of the head and the upper jaw are always in a fixed positional relationship with respect to each other. Inner body structures are particularly useful, because they are in most cases not covered by skin, which shifts easily, and thus retain their outer form under normal circumstances.

In one embodiment of the invention, the registration area on the actual patient's body or portion of the patient's body is measured by means of a surface scanner which in particular comprises a scanner probe which can be positionally located and/or tracked. The position and orientation of the probe can then be established by a tracking system which determines the actual spatial position of at least a part of the body or body portion. The tracking system can be a medical tracking system, such as a camera tracking system or a magnetic tracking system or the like. It can of course be used in association with the medical navigation system, in order to provide the latter with actual 3D position data.

A surface scanner as mentioned above can also comprise a surface data recording and/or processing unit which creates a positionally determined surface model of the registration area.

The method of the present invention can be performed in such a way that the registration area is measured by means of spaced interferometric measurements, in particular using a thin film interference scanner.

The method according to the present invention can also be supplemented by manually acquiring at least one additional registration landmark on the actual patient's body or body portion and including it in the assignment process by assigning it to a respective position in the image. This can serve to confirm the registration result, in particular the common angular orientation of the actual registration area and the registration area in the image.

In an alternative or additional embodiment, at least one additional registration point or landmark on a frame which is placed on the actual patient's body or body portion can be acquired and included in the assignment process by assigning it to a corresponding related position, in particular a calculated position, in the image in order to supplement the registration process or to confirm the registration result, in particular the common angular orientation of the actual registration area and the registration area in the image.

In the latter case, the registration area on the actual patient's body or body part can be measured by means of a positionally determined surface scanner which in particular comprises a scanner probe which is fixedly attached to the frame, wherein the scanner and/or the frame can be positionally located and/or tracked by a tracking system which determines the actual spatial position of at least a part of the body or body portion.

The medical registration device in accordance with the present invention, which can be used in a registration method as described above, comprises a surface scanner for scanning a registration area comprising the surface of a substantially rigid body structure, in particular an inner structure, made of bone or cartilage. The scanner can be designed as a surface scanner, in particular an inner surface scanner, comprising a scanner probe which can be positionally located and/or tracked and in particular used for inserting into and/or scanning the surface of one or more of the following body structures:

the meatus or ear channel, or at least a part of the meatus, in particular the outer meatus;
 the palate, in particular the bony or hard palate;
 the upper inner jaw area and/or lower inner jaw area;
 the inner nose cartilage structure.

The scanner can be embodied as an interferometric measurement scanner, in particular a thin film interference scanner.

In particular embodiments of the present invention, the registration device can be fixed to:

a fixation support for the actual body or body portion; or
 a frame on the actual patient's body or body portion, wherein the frame is positionally acquired and included in the assignment process by assigning it to a corresponding related position, in particular a calculated position, in the image in order to supplement the registration process or to confirm the registration result, in particular the common angular orientation of the actual registration area and the registration area in the image.

The invention also relates to a program which, when it is running on a computer or is loaded onto a computer, causes the computer to perform a method such as has been described above in various embodiments. The invention also relates to a computer program storage medium which comprises such a computer program.

The invention will now be explained in more detail by referring to particular embodiments and to the attached drawings. It is to be noted that each of the features of the present invention as referred to here can be implemented separately or in any expedient combination. In the drawings:

FIG. 1 schematically shows how the surface of an ear channel (meatus) is scanned by means of a scanner probe;

In the embodiments explained below, an automatic cranial patient registration process using special, surface-measuring earplugs will be described, wherein a three-dimensional surface measurement of the ear channel is used to automatically register the patient to a cranial data set, in particular a segmented data set. The embodiments shown are based on accurately measuring the inner surface of the (outer) meatus.

Thin film interference measurements can be used to model the surface of the ear channel, and such methods are for example described in the article "Emission reabsorption laser induced fluorescence (ERLIF) film thickness measurement" by Carlos H. Hidrovo and Douglas P. Hart (in: Measurement Science and Technology 12 (2001), pages 467 to 477). The measurement method discussed in said article can of course utilise the present invention.

Figure 1:
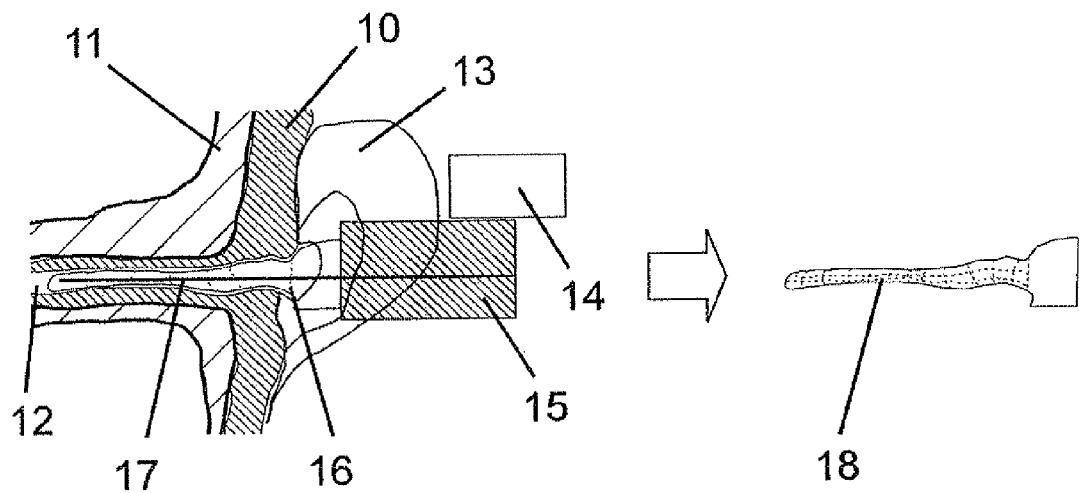

As shown in the general depiction of FIG. 1, the technique used in accordance with one embodiment of the present invention employs an oil-filled balloon 16 which is inserted through the outer ear 13 into the meatus 12. The balloon is filled with oil in such a way that it completely covers the inner surface of the meatus 12. An interferometric device or probe 17 which is inserted into the oil-filled balloon 16 allows an exact three-dimensional reconstruction of the balloon's shape to be created or acquired and therefore yields a three-dimensional model 18 of the outer meatus which in particular includes information about the relative position of the support 15 and the probe 17 which is fixedly attached to the support 15. In an interferometric measuring method, the probe 17 inside the balloon 16 is made of a solid material which conducts laser light and has a rigid connection to the measuring device support 15 and a reference element 14 attached to the support 15.

Other methods for mapping the three-dimensional surface of the meatus 12 can also be used, for example methods which are used for modelling hearing aids to the individual meatus of a patient.

A software can be used to reconstruct (determine) the inner surface of the meatus 12 in a given data set (for example, a diagnostic CT or MR image data set) of the patient, for example using atlas segmentation methods. Since the inner part of the meatus 12 consists of bony edges 11 and also tissue edges 10 on the outer portion, it should be possible to obtained a good MR and/or CT image. The segmented data set model (or models) and the ear measurement model can be aligned using standard three-dimensional alignment algorithms, thus yielding a transformation matrix between the measuring device and the patient data set co-ordinate system. It is this transformation matrix which serves as the basis for the registration sought.

The measuring interferometric device support 15 can be used together with a tracking or referencing element 14 mounted to it. Tracking the units simultaneously, with the reference element 14 associated with a tracking system (not shown), allows the co-ordinate systems of the patient data and the tracking system to be registered. The measuring device or its support 15 is preferably then mounted rigidly to the reference element 14 itself. The measuring apparatus is thus rigidly fixed to the patient and the (electromagnetic or optical) reference element 14 which is tracked by a tracking system which is connected to a navigation system. Since at least the fixation or the relative position between the support 15 and the reference element 14 is known by design or calibration, the patient data can be directly referenced to the reference element co-ordinate system.

Figure 2:
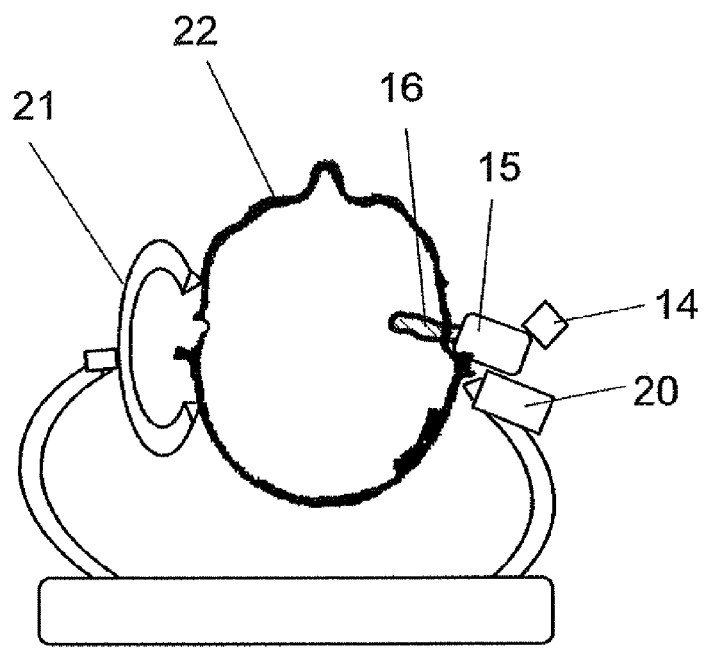
FIG. 2 shows a scanning set-up including a head clamp.

FIG. 2 shows the set-up of FIG. 1 when integrated with a head clamp 21, for example a Mayfield head clamp, for cranial operation purposes. The support 15 is fixed to one of the screws 20 of the head clamp 21 which in turn rigidly fixes the head. The reference element 14 (for example, an optical or magnetic tracking device) is fixed to the support 15 and the measuring device which itself has a positionally defined connection to the measuring probe 16 inside the meatus 12. Since the specific position of the measuring device and its components (the support 15 and the probe 16) is known by means of the reference element 14, the measured surface of the meatus 12 can be assigned to a unique position, location and orientation. As mentioned above, aligning said positionally determined shape to the respective shape in the image data of the patient yields a registration transformation matrix.

Measuring and tracking as described above yields the correct and accurate registration which is the aim of the present invention. Registration results can be confirmed or registration can even be supplemented, in particular with regard to the rotational orientation of the inner ear anatomy, using the embodiments of the present invention shown in FIGS. 3 to 5.

Figure 3:
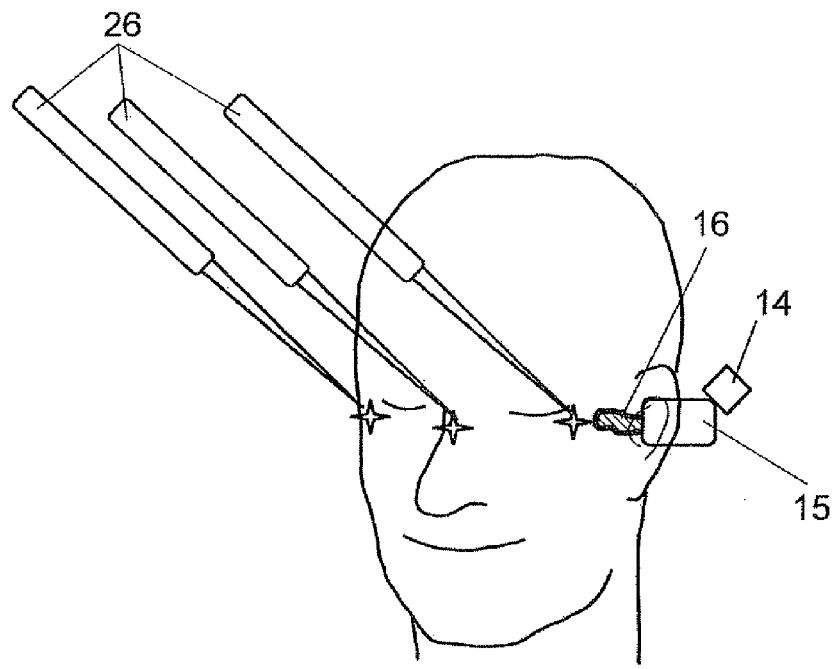
FIG. 3 shows additional landmark points being acquired by means of a pointer.

FIG. 3 shows how additional landmark points are collected using a magnetically or optically tracked pointer instrument 26. The landmarks are points on the eye canthus or the nasion, and their positions in the patient data set can be calculated using automatic atlas segmentation algorithms. Such algorithms are known as a way of acquiring typical facial landmarks such as the nasion or the canthus of the eyes. The acquired points can then be used in the alignment procedure as additional constraints when aligning the surface of the three-dimensional model 18 with the measured model of the meatus 12.

Figure 4:
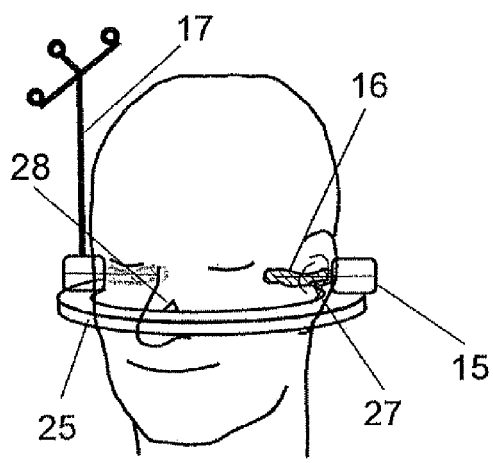
FIGS. 4 and 5 show a frame being additionally used for registration purposes.
Figure 5:
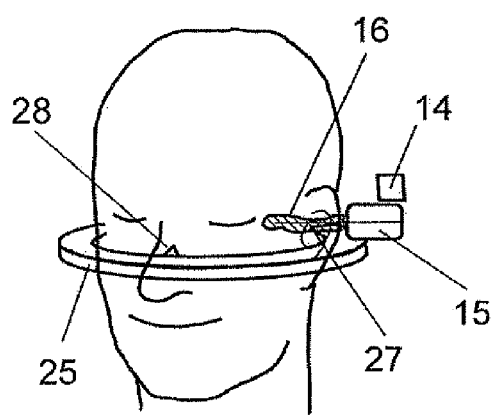

FIGS. 4 and 5 show another way of providing additional orientation data, by attaching a frame 25 to the reference element, i.e. an optical reference element 17 (FIG. 4) or an electromagnetic reference element 14 (FIG. 5). The frame 25 is constructed in such a way that it rigidly holds the ear measuring apparatus support 15 on one or both sides and additionally has defined points which anatomically fit into the ear 27 or onto the nasion 28. The frame is rigidly attached to the respective reference device 14, 17, and matching the three calibrated points on the ears and the nasion to landmarks—defined, for example, using atlas segmentation—allows additional constraints to be used in the registration calculation.

The invention claimed is:

1. A medical image registration method in which a portion of a patient's body is positionally registered to a patient image data set created using an associated medical body-imaging technique such as MR, CT or x-ray imaging, the method comprising:

establishing, by an associated tracking system, an actual spatial position of at least a part of the body or body portion of the patient by determining the actual spatial position of the at least a part of the body or body portion, wherein the part of the body or body portion comprises a registration area in the form of the surface of a substantially rigid body structure, such as an inner structure, made of bone or cartilage; and assigning, in an associated medical navigation system, the actual spatial position to a respective position in an image of the patient in the patient image data set;

wherein at least one additional registration point or landmark on a frame which is placed on the actual patient's body or body portion is acquired and included in the assigning by assigning the at least one additional registration point or landmark on the frame to a corresponding related position in the image of the patient in the patient image data set in order to supplement or to confirm a registration result, wherein the registration area on the actual patient's body or body part comprises a three-dimensional surface of a channel measured by means of an associated positionally determined interferometric surface measurement scanner which comprises a scanner probe which is fixedly attached to the frame and selectively inserted into the channel, wherein at least one of the scanner and the frame are configured to be selectively positionally located or tracked by the associated tracking system which determines the actual spatial position of the at least a part of the body or body portion.

2. The method according to claim 1, wherein the registration area comprises the surface of one or more of the following body structures:

the meatus or ear channel, or at least a part of the meatus, in particular the outer meatus;

the bony palate or hard palate;

at least one of the upper inner jaw area and the lower inner jaw area;

the inner nose cartilage structure.

3. The method according to claim 1, wherein the registration area on the actual patient's body or portion of the patient's body is measured by means of the associated surface scanner which comprises the scanner probe which can be at least one of positionally located and tracked.

4. The method according to claim 1, wherein a position and orientation of the scanner probe can be established by the associated tracking system.

5. The method according to claim 1, wherein the interferometric surface measurement scanner comprises a surface data recording and processing unit which creates a positionally determined surface model of the registration area.

6. The method according to claim 1, wherein the interferometric surface measurement scanner is a thin film interference scanner.

7. The method according to claim 1, wherein at least one additional registration landmark on the actual patient's body or body portion is manually acquired and included in the assigning by assigning it to a respective position in the patient image data set in order to at least one of supplement or confirm the registration result.

8. A medical image registration device by means of which a portion of an associated patient's body is positionally registered to a patient image data set created using an associated medical body-imaging technique such as MR, CT or x-ray imaging, the device comprising:

a tracking system establishing an actual spatial position of at least a part of the body or body portion of the patient by determining the actual spatial position of the at least a part of the body or body portion;

a medical navigation system assigning the actual spatial position to a respective position in an image of the patient in the patient image data set; and a positionally determined interferometric surface measurement scanner for scanning a registration area comprising a scanner probe which is configured to be selectively inserted into a channel of a substantially rigid body structure, such as an inner structure, made of bone or cartilage, of the associated patient's body or body part.

9. The device according to claim 8, wherein the scanner probe can be at least one of positionally located and tracked and used for at least one of inserting into and scanning the surface of one or more of the following body structures:

the meatus or ear channel, or at least a part of the meatus, in particular the outer meatus;

at least one of the bony palate or the hard palate;

at least one of the upper inner jaw area and the lower inner jaw area;

the inner nose cartilage structure.

10. The device according to claim 8, wherein the interferometric surface measurement scanner is a thin film interference scanner.

11. The device according to claim 8, wherein the device is fixed to:
- a fixation support for the associated patient's body or body portion; or
- a frame on the associated patient's body or body portion, wherein the frame is positionally acquired and included in the assigning by assigning the frame to a corresponding related position in the image of the patient in the patient image data set in order to supplement or to confirm a registration result.

12. A computer program embodied on a non-transitory computer readable medium which, when it is running on a computer or is loaded onto a computer, causes the computer to perform a medical image registration method in which a portion of a patient's body is positionally registered to a patient image data set created using an associated medical body-imaging technique such as MR, CT or x-ray imaging, the method comprising:
- establishing, by an associated tracking system, an actual spatial position of at least a part of the body or body portion of the patient by determining the actual spatial position of the at least a part of the body or body portion, wherein the part of the body or body portion comprises a registration area in the form of the surface of a substantially rigid body structure, such as an inner structure, made of bone or cartilage; and
- assigning, in an associated medical navigation system, the actual spatial position to a respective position in an image of the patient in the patient image data set;
- wherein at least one additional registration point or landmark on a frame which is placed on the actual patient's body or body portion is acquired and included in the assigning by assigning the at least one additional registration point or landmark on the frame to a corresponding related position in the image of the patient in the patient image data set in order to supplement or to confirm a registration result,
- wherein the registration area on the actual patient's body or body part comprises a three-dimensional surface of a channel measured by means of an associated positionally determined interferometric surface measurement scanner which comprises a scanner probe which is fixedly attached to the frame and selectively inserted into the channel,
- wherein at least one of the scanner and the frame are configured to be selectively positionally located or tracked by the associated tracking system which determines the actual spatial position of the at least a part of the body or body portion.

13. A non-transitory computer program storage medium which stores the computer program according to claim 12.

14. A method in a medical navigation system for automatic cranial registration of an associated patient, the method comprising:
- storing in a non-transient storage medium of the medical navigation system a three-dimensional model of a registration area of the associated patient including an inner channel of the associated patient, the model being acquired using a probe of an associated surface scanner system being disposed in the inner channel of the associated patient, the probe of the associated surface scanner system scanning the inner channel to develop the three-dimensional model of the registration area;
- imaging, by the medical navigation system, a portion of the associated patient to obtain a patient image data set of the patient, wherein one or more physical structures of the associated patient are represented in the patient image data set relative to a coordinate system of the patient image data set, wherein the portion of the associated patient comprises the registration area including the inner channel of the associated patient; and
- determining, by a processor of the medical navigation system, a transformation matrix between the associated surface scanner system and the coordinate system of the patient data set by aligning the three-dimensional model of the inner channel of the associated patient with a respective portion of the patient image data set corresponding to the inner channel of the associated patient.

* * * * *